United States Patent
Kamigiri et al.

(10) Patent No.: US 7,030,085 B2
(45) Date of Patent: Apr. 18, 2006

(54) THIOPEPTIDE COMPOUNDS (75) Inventors: Kazuma Kamigiri, Itabashi-ku (JP); Masato Watanabe, Itabashi-ku (JP); Koji Nagai, Itabashi-ku (JP); Nakako Arao, Itabashi-ku (JP); Kenichi Suzumura, Tsukuba (JP); Ken-ichi Suzuki, Itabashi-ku (JP); Ryuichiro Kurane, Matsudo (JP); Masakazu Yamaoka, Tsukuba (JP); Yasuhiro Kawano, Tsukuba (JP)

(73) Assignees: Astellas Pharma INC, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 42 days.

(21) Appl. No.: 10/471,873

(22) PCT Filed: Mar. 12, 2002

(86) PCT No.: PCT/JP02/02305

§ 371 (c)(1),
(2), (4) Date: Sep. 15, 2003

(87) PCT Pub. No.: WO02/072617

PCT Pub. Date: Sep. 19, 2002

(65) Prior Publication Data

US 2004/0097702 A1 May 20, 2004

(30) Foreign Application Priority Data

Mar. 13, 2001 (JP) ............................. 2001-070705

(51) Int. Cl.
*A01N 37/18* (2006.01)
*A61K 38/00* (2006.01)
*A61K 31/33* (2006.01)
*C12P 21/04* (2006.01)
*C12N 1/20* (2006.01)

(52) U.S. Cl. .............................. 514/9; 514/2; 514/183; 435/71.3; 435/252.5

(58) Field of Classification Search ................... 514/2, 514/9, 183; 435/71.3, 252.5
See application file for complete search history.

(56) References Cited

FOREIGN PATENT DOCUMENTS

WO    WO 97/48408 A2    12/1997

OTHER PUBLICATIONS

Shoji J. et al., Isolation of Three New Antibiotics, Thiocillins I, II, and III, Related to Micrococcin P (Studies on Antibiotics from the Genus *Bacillus*. VIII), J, Antibiotics, Apr. 1976, vol. 29, No. 4, pp. 366 to374.

Shoji J. et al., "Structural Studies on Thiocillins I, II and III (Studies on Antibiotics from the Genus *Bacillus*. XXIX)", J, Antibiotics, Sep. 1981, vol. 34 No. 9, pp. 1126 to 1136.

Bycroft B.W. et al., "The Structures of the Highly Modified Peptide Antibiotics Micrococcin $P_1$ and $P_2$", J.C.S. Chem. Comm., 1978, No. 6, pp. 256 to 258.

Ciufolini M.A. et al., "Synthesis of the Bycroft-Gowland Strucutre of Micrococcin P1", Organic Letters, 1999, vol. 1, No. 11, pp. 1843 to 1846.

*Primary Examiner*—Irene Marx
*Assistant Examiner*—Lora E Barnhart
(74) *Attorney, Agent, or Firm*—Sughrue Mion, PLLC (57) ABSTRACT

A microorganism belonging to the genus *Bacillus* is cultured and thiopeptide compounds QN3323 and thiocillin I/II compounds are collected from the culture medium. The compounds are useful as drugs to treat infections caused by multidrug-resistant bacteria.

9 Claims, 2 Drawing Sheets

THIOPEPTIDE COMPOUNDS

TECHNICAL FIELD

The present invention relates to remedies for infections with multidrug-resistant bacteria such as MRSA and VRE, which comprise a thiopeptide compound as the active ingredient thereof. It also relates to novel thiopeptide compounds QN3323 and their production, and to drugs that contain any of the compounds as an active ingredient thereof.

Heretofore well known are various antibiotics that are produced by microorganisms, including, for example, β-lactam antibiotics such as penicillin, cephalosporin, carbapenem; macrolide antibiotics such as erythromycin, josamycin, rokitamycin; and aminoglycoside antibiotics such as kanamycin, gentamycin, tobramycin, etc. Some of these antibiotics and chemically modified derivatives thereof are extremely effective as bactericides and antibacterials and many of them are now actually in clinical use.

Recently, however, methicillin-resistant *Stayphylococcus aureus* (hereinafter referred to as MRSA) having high resistance to these antibiotics has frequently appeared in the field of clinical medicine, and it is now a serious social problem. In 1996, in addition, it was reported in Japan that enterococci highly resistant to vancomycin, that has been widely used to treat infections caused by MRSA (vancomycin-resistant *Enterococcus*—hereinafter referred to as VRE), were isolated from a clinical case. Apart from these, some types of *Pseudomonas aeruginosa* and *Klebsiella pneumoniae* are known to have high resistance to various drugs. These bacteria are referred to as multidrug-resistant bacteria, and are now specifically problematic in the field of clinical medicine. Therefore, it is much desired to develop antibiotics that are effective against such multidrug-resistant bacteria.

Macrocyclic compounds having a thiazole as the ring constitutive component are generically referred to as thiopeptide compounds, and various compounds of this type have been reported. They differ, for example, in the number of the ring-constituting atoms in them and in the elements that constitutes their rings. Concretely, there are reported monocyclic macrocyclic-structured compounds such as thiocillin I, and tricyclic macrocyclic-structured compounds such as glycothiohexide-α (*J. Antibiotics* 47: 894, 1994), and they differ in their ring structures. Thiocillin I, thiocillin II and micrococcin P2 are compounds having a monocyclic macrocyclic structure in common, and their antibacterial activity against gram-positive bacteria has been reported (*J. Antibiotics* 29: 366–374, 1976; *J. Chem. Soc., Chem. Commun.*, 1978(6), 256–8; International Patent Publication WO97/48408). However, no report has heretofore been made until now relating to the antibacterial activity of these compounds against multidrug-resistant bacteria such as MRSAT and VRE.

Regarding thiopeptide compounds, anti-MRSA or anti-VRE activity of glycothiohexide α (*J. Antibiotics* 47:894, 1994), amythiamicin A (*J. Antibiotics* 47: 668, 1994; ibid. 47:1153, 1994), sulfomycin (*J. Nat. Prod.*, 62:1562, 1999) and promoinducin (*Biosci. Biotechnol. Biochein.* 59:876, 1995) has been reported. Glycothiohexide α is a compound having a tricyclic macrocyclic structure. Amythiamicin A, sulfomycin and promoinducin have a monocyclic macrocyclic structure, but differ from the above-mentioned thiocillins in the type of amino acids that constitute their rings, and, in addition, the number of atoms that constitute the ring of the former macrocyclic compounds is larger than that of thiocillins.

We, the present inventors have conducted research to identify antibiotics produced by naturally existing microorganisms, and, as a result, have found that cells of a type that belong to the genus *Bacillus* may produce compounds having an antibacterial activity against bacteria that include multidrug-resistant bacteria such as MRSA and VRE. Further, we have studied in detail the culture of the cells and have succeeded in isolating novel thiopeptide compounds QN3323-A, QN3323-B and QN3323-Y1 and known thiopeptide compounds thiocillin I, thiocillin II and micrococcin P2 from the culture of the cells, and, in addition, have found that these compounds have anti-MRSA activity and anti-VRE activity, and have completed the present invention.

Specifically, the invention relates to remedies for infections with multidrug-resistant bacteria, especially those for infections with MRSA or VRE, which contain, as an active ingredient thereof, a thiopeptide compound of the following formula (I) or a pharmaceutically acceptable salt thereof.

(I)

wherein A represents CH—OH or C=O; R represents H or CH$_3$; R' represents H or OH.

The invention also relates to a method for producing the thiopeptide compounds, which comprises cultivating cells of *Bacillus* sp. QN03323 (FERM BP-7864) that belongs to the genus *Bacillus* followed by collecting the thiopeptide compounds of formula (I) from the culture of the cells.

The invention further relates to novel thiopeptide compounds of the following formula (I') or their pharmaceutically acceptable salts:

(I')

wherein A represents CH—OH or C=O; R represents H or CH$_3$; R$^a$ and R$^b$ each represent H or CH$_3$;

provided that when R$^a$ is H, then R$^b$ is CH$_3$; when R$^a$ is CH$_3$, then R$^b$ is H; when A is CH—OH, then R$^a$ is H and R$^b$ is CH$_3$.

Preferred are the following compounds:

(1) A is C=O; R is H; R$^a$ is CH$_3$; and R$^b$ is H (QN3323-A), (2) A is C=O; R is CH$_3$; R$^a$ is CH$_3$; and R$^b$ is H (QN3323-B), and (3) A is CH—OH; R is H; R$^a$ is H; and R$^b$ is CH$_3$ (QN3323-Y1).

The invention still further relates to a method for producing the thiopeptide compounds, which comprises cultivating microorganisms belonging to the genus *Bacillus* and having the ability to produce the thiopeptide compounds of formula (I'), followed by collecting the thiopeptide compounds from the culture of the cells.

The invention still further relates to a medicine, especially an antibacterial agent that contains, as the active ingredient thereof, the thiopeptide compound of formula (I') or its pharmaceutically acceptable salt.

The invention is described in detail hereinunder.

The thiopeptide compounds (I) of the invention are obtained by an ordinary method that comprises cultivating cells belonging to the genus *Bacillus* and having the ability to produce the compounds in a nutrient medium followed by collecting the compounds from the culture where the compounds have accumulated. The microorganisms that are used in the method of producing the compounds may be any that belong to the genus *Bacillus* and have the ability to produce the compounds. One example of the microorganisms of the type useful for the method is a gram-positive strain QN03323 belonging to the genus *Bacillus*, which was separated from unidentified sponge collected at the seaside of Taketomi-cho, Yaeyama-gun, Okinawa-ken (Iriomote Island). The bacterial properties of the strain are as follows:

1) Morphological Property:

This strain is a gram-positive *bacillus* and is motile. The size of the cell is from 1 to 1.7×5 to 8 μm. One cell has one oval spore formed therein.

2) Cultural Property:

This strain forms white colonies on a meat extract agar medium. Each colony is circular, its surface is not glossy, and its periphery is rough. In static culture in meat extract broth, the culture with the cells growing therein is completely cloudy or the cells sink down, and no film is formed on the surface of the medium. In stab culture in broth gelatin, the cells liquefy the gelatin. In culture with litmus milk, the culture is peptonized and is neutral, and this is not coagulated.

3) Physiological Property:

The physiological property of QN03323 is as follows:

| Nitrate Reduction | positive | Dinitrification | negative |
|---|---|---|---|
| MR Test | negative | VP Test | positive |
| Indole Production | negative | Hydrogen Sulfide Production | negative |
| Starch Hydrolysis | positive | Citric Acid Utilization | negative |
| Nitrate Utilization | negative | Ammonium Salt Utilization | negative |
| Water-Soluble Fluorescent Dye Production | negative | Urease | positive |
| Oxidase | positive | Catalase | negative |
| Growing Temperature Range | 10 to 45° C. | Optimum Growing Temperature | 28 to 40° C. |

| | | | |
|---|---|---|---|
| pH Range for Growth | pH 5 to 9 | Optimum pH for Growth | pH 6 to 8 |
| Growth under Anaerobic Condition | positive | Arginine Dihydrolase | positive |
| Growth in 3% NaCl-added broth medium | | positive | |
| Growth in 6% NaCl-added broth medium | | positive | |

(Production of Acid from Saccharide)

| | | | |
|---|---|---|---|
| L-arabinose | negative | D-galactose | negative |
| D-xylose | negative | Maltose | positive |
| D-glucose | positive | Trehalose | positive |
| D-mannose | positive | Lactose | negative |
| D-fructose | positive | D-sorbitol | negative |
| Sucrose | positive | Glycerin | positive |
| Inositol | negative | Starch | positive |
| D-mannitol | negative | | |

The above-mentioned mircrobial properties of the strain are summarized. The strain is a gram-positive facultative anaerobic *bacillus*, and is motile. Its growth temperature range falls between 10 and 45° C.; it is positive in nitrate reduction, starch hydrolysis, urease, oxidase test, gelatin liquefying reaction and arginine dihydrolase; and it produces acid from D-glucose, D-mannose, D-fructose, sucrose, maltose, trehalose, glycerin and starch. On the other hand, it is negative in denitrification, indole production, hydrogen sulfide production, citric acid utilization, inorganic nitrogen source utilization and catalase test.

Based on the above-mentioned properties thereof, the strain was looked up in *BERGEY's Manual of Systematic Bacteriology*, 1989 and other references, and, as a result, it was identified as a type of bacteria belonging to the genus *Bacillus*, and was named *Bacillus* sp. QN03323.

This strain, *Bacillus* sp. QN03323, has been deposited with the National Institute of Advanced Industrial Science and Technology, International Patent Organism Depositary Center (Tsukuba Central 6, 1—1—1, Higashi, Tsukuba, Ibaraki, Japan, 305-8566) as FERM BP-7864 (as of deposition date, Feb. 14, 2001). In general, microorganisms may artificially or naturally mutate. Therefore, *Bacillus* sp. QN03323 for use in the invention shall include not only the microorganisms separated from natural matters but also those artificially mutated from them through exposure to UV rays, radiations or chemicals and their natural mutants.

(Production Method)

The compounds of the invention may be obtained by cultivating the microorganisms belonging to the genus *Bacillus* and having the ability to produce the compounds of the invention. The cultivation of the microorganisms may be effected in any ordinary manner of cultivating ordinary microorganisms.

The medium to be used for the cultivation may be any one that contains nutrient sources for the microorganisms having the ability to produce the compounds of the invention (e.g., *Bacillus* sp. QN03323). For example, it may be any of synthetic media, semi-synthetic media or natural media. Regarding the composition of the medium, the carbon source thereof includes, for example, L-arabinose, D-xylose, D-glucose, D-fructose, sucrose, inositol, L-rhamnose, raffinose, D-mannitol, mannose, melibiose, lactose, D-galactose, maltose, trehalose, salicin, xanthine, chitin, starch, glucose, dextrin, glycerin, and vegetable oil; and the nitrogen source thereof includes, for example, broth, peptone, gluten meal, cotton seed refuse, soybean meal, peanut meal, fish meal, corn steep liquor, dry yeast, yeast extract, ammonium chloride, ammonium sulfate, ammonium nitrate, uric acid and other organic and inorganic nitrogen compounds. Metal salts may be optionally present in the medium, including, for example, sodium, potassium, magnesium, calcium, zinc, iron or cobalt sulfates, nitrates, carbonates and phosphates.

Further if desired, the medium may also contain growth promoters or defoaming agents such as methionine, cysteine, cystine, thiosulfates, methyl oleate, lard oil, silicone oil and surfactant.

Preferably, the cells are cultivated under an aerobic conditions. The temperature for cultivation may fall between 10 and 45° C., preferably between 25 and 30° C. or so. The pH of the medium may fall approximately between 5 and 9, preferably approximately between 6 and 8 for better results. The cultivation period can be suitably determined depending on the composition of the medium used and the temperature for cultivation. In general, it may be approximately from 1 to 20 days, preferably approximately from 2 to 5 days.

For isolating and purifying the compounds of the invention from the culture, any ordinary method of isolating and purifying physiological substances from ordinary microbial cultures can be employed. For example, the intended compounds are extracted out of the culture with a suitable solvent, and the effective substances are isolated and purified from the resulting extracts. Concretely, based on the antibacterial activity thereof as the index for isolation and purification thereof, the compounds of the invention may be isolated and purified by any ordinary method that is used in producing ordinary physiologically active substances by utilizing the solubility and the solubility difference of the substances in suitable solvents. These methods may be used singly, if desired, or may be combined in any desired manner for repetition.

The compounds of the invention may form acid addition salts, and the salts are pharmaceutically acceptable salts. Concretely, they include acid-addition salts with inorganic acids such as hydrochloric acid, hydrobromic acid, hydroiodic acid, sulfuric acid, nitric acid, phosphoric acid; or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid. The salts of the compounds of the invention may be obtained in any ordinary salt formation from the compounds of the invention that have been isolated and purified or during the stage of isolation and purification of the compounds from the cultures.

The thiopeptide compounds (I) or their pharmaceutically acceptable salts of the invention have an asymmetric carbon and a double bond, and therefore include optical isomers and geometrical isomers based on these. The compounds of the invention encompass mixtures of these isomers and isolated isomers. Further, the invention also encompasses various hydrates and solvates of the thiopeptide compounds (I) or their pharmaceutically acceptable salts, as well as their crystals and crystal polymorphic substances. The compounds of the invention include pharmaceutically acceptable prodrugs thereof. The pharmaceutically acceptable prodrugs are compounds that have a group capable of being convened into OH or the like in the compounds of the invention through solvolysis or under physiological conditions. The groups capable of forming such prodrugs are described in, for example, *Prog. Med.*, 6, 2157–2161 (1958); *Pharmaceutical Research and Development* (by Hirokawa Publishing Company, 1990), Vol. 7, Drug Design, 163–198.

INDUSTRIAL APPLICABILITY

The compounds (I) of the invention have antibacterial activity against multidrug-resistant bacteria such as MRSA and VRE, and are therefore useful as remedies for infections with multidrug-resistant bacteria, especially for infections with MRSA or VRE. The novel compounds (I') of the invention are useful as active ingredients for pharmaceutical preparations. In particular, since they have antibacterial activity, they are useful as antibacterial agents.

The pharmaceutical preparations that contain, as the active ingredient thereof, one or more of the compounds or their salts of the invention may be prepared by the use of carriers, vehicles and other additives that are generally used in formulating ordinary pharmaceutical preparations.

The administration route for the preparations may be any of oral administration with tablets, pills, capsules, granules, powders or liquids, or parenteral administration with intravenous or intramuscular injections, suppositories, subcutaneous preparations, nasal preparations or inhalations.

The solid composition for oral administration in the invention includes tablets, powders and granules. In such solid compositions, one or more active substances are mixed with at least one inert vehicle such as lactose, mannitol, glucose, hydroxypropyl cellulose, microcrystalline cellulose, starch, polyvinylpyrrolidone, magnesium metasilicate aluminate. In an ordinary manner, the compositions may contain any inert additives, for example, a lubricant such as magnesium stearate a disintegrator such as sodium carboxymethyl starch, and a dissolution promoter. Optionally, the tablets and the pills may be coated with a sugar film or with a gastric-soluble or intestinal-soluble coating agent.

The liquid compositions for oral administration may include pharmaceutically acceptable emulsions, liquids, suspensions, syrupds, elixirs, as well as any other ordinary inert solvent such as pure water and ethanol. Apart from such an inert solvent, the composition may further contain auxiliary agents such as solubilizers, wetting agents, suspending agents, as well as sweeteners, flavorings, aromas, and preservatives.

The injections for parenteral administration contain germ-free aqueous or non-aqueous liquids, suspensions or emulsions. The aqueous solvent may be, for example, distilled water for injections and physiological saline. The non-aqueous solvent includes, for example, propylene glycol, polyethylene glycol, vegetable oil such as olive oil, alcohols such as ethanol, and Polysorbate 80 (trade name). These compositions may further contain isotonizers, preservatives, wetting agents, emulsifiers, dispersants, stabilizers and dissolution promoters. These are sterilized, for example, through filtration through bacteria-trapping filters, or through addition of bactericide thereto, or through irradiation. As the case may be, germ-free solid compositions are prepared, and they may be dissolved or suspended in germ-free water or germ-free solvent for injections before use.

The dose of the active ingredient compound in the invention may be suitably determined, depending on the condition, the age and the sex of the cases to which it is administered, but is, in general, approximately from 0.1 to 1000 mg/adult/day for oral administration, and is approximately from 0.1 to 500 mg/adult/day for parenteral administration. This may be administered all at a time or in multiple times. The dose shall vary depending on various conditions.

BEST MODES OF CARRYING OUT THE INVENTION

The invention is described in more detail with reference to the following Examples. The compounds of the invention should not be limited to those in the following Examples.

EXAMPLE 1

A medium containing 10 g of glucose, 20 g of potato starch, 5 g of polypeptone, 5 g of yeast extract, 4 g of calcium carbonate and 1 liter of distilled water (having a pH of 7.0 before sterilization) was prepared, put into 500-ml Erlenmeyer flasks with 100 ml each therein, and sterilized at 121° C. for 20 minutes. The cells of *Bacillus* sp. QN03323 that had been grown on a Bennett-agar medium were scraped out and inoculated onto the medium, and cultivated with shaking at 220 rpm at 28° C. for 3 days to prepare a seed culture. Next, a medium containing 5 g of glucose, 5 g of Bactopeptone (by Difco), 2 g of yeast extract and 1 liter of distilled water (having a pH of 7.5 before sterilization) was prepared and put into 500-ml Erlenmeyer flasks with 100 ml each therein. 100 flasks with the medium therein were thus prepared, and these were sterilized at 121° C. for 20 minutes. 2 ml of the seed culture was inoculated onto the medium of every flask, and cultivated with shaking at 220 rpm at 28° C. for 3 days.

Thus cultivated, 10 liters of the culture was controlled to have a pH of 7.0, to which was added 40 liters of acetone. The resulting extract was well stirred, and filtered, and acetone was removed from it under reduced pressure. 12 liters of ethyl acetate was added to it, and well stirred, and the ethyl acetate layer was concentrated under reduced pressure. Then, ethyl acetate was removed from it. The residue was subjected to column chromatography with Sephadex LH-20 (by Amersham Pharmacia Biotec, ϕ30 ×350 mm), and developed with N-hexane/dichloromethane/methanol (4/5/1) to obtain an active fraction. The active fraction was subjected to silica gel thin-layer chromatography (with Kieselgel 60F254, 20 mm×20 mm, by Merck), developed with chloroformlmethanol (15/1), and the active fraction was scraped out. The active fraction was then subjected to ODS column chromatography (ϕ20×250 mm, Develosilpack, by Nomura Chemical), and an active substance to give a peak was fractionated with an elution solvent of aqueous 70% methanol solution, at a flow rate of 9.0 ml/min and a detection wavelength of 210 nm. From it, the compounds of the invention, QN3323-A (5.0 mg) and QN3323-B (1.5 mg) were isolated. Similarly, known compounds, thiocillin I (11 mg) and thiocillin II (5.3 mg) were isolated.

EXAMPLE 2

100 liters of a culture that had been obtained in the same manner as in Example 1 was centrifuged, and the supernatant was subjected to column chromatography with Diaion HP-20 (by Mitsubishi Chemical) (10 liters). The deposit was extracted with aqueous 80% acetone solution (25 liters) and concentrated under reduced pressure to remove acetone. Then, this was again subjected to column chromatography with Diaion HP-20 as above. The HP-20 column was washed with water (30 liters) and aqueous 30% acetone solution (30 liters), and then eluted with aqueous 90% acetone solution (30 liters). The eluate fraction was concentrated under reduced pressure to remove acetone through evaporation. The resulting concentrate was extracted twice with 10 liters of ethyl acetate, and the ethyl acetate layer was concentrated to dryness under reduced pressure. The resulting solid was then subjected to silica gel column chromatography (with Kieselgel 60 by Merck, φ65 mm×130 mm), and eluted with chloroform/methanol (9/1 and 5/1) solutions. The active fraction was concentrated, and then subjected to middle-pressure silica gel column chromatography (ULTRAPACK SI-40C by Yamazen, φ37 mm×300 mm), and eluted with chloroform/methanol (20/1) solution to fractionate active fractions. This contained QN3323-A (91.7 mg), QN3323-B (27.3 mg), QN3323-Y1 (161 mg), thiocillin I (870 mg) and thiocillin II (305.5 mg).

The active fraction obtained through the middle-pressure silica gel column chromatography was further subjected to ODS HPLC (Develosil C30 UG-5 by Nomura Chemical, φ20 mm×250 mm), and eluted with aqueous 50% acetonitrile solution to fractionate active fractions. This is micrococcin P2 (4.1 mg).

Figure 1:
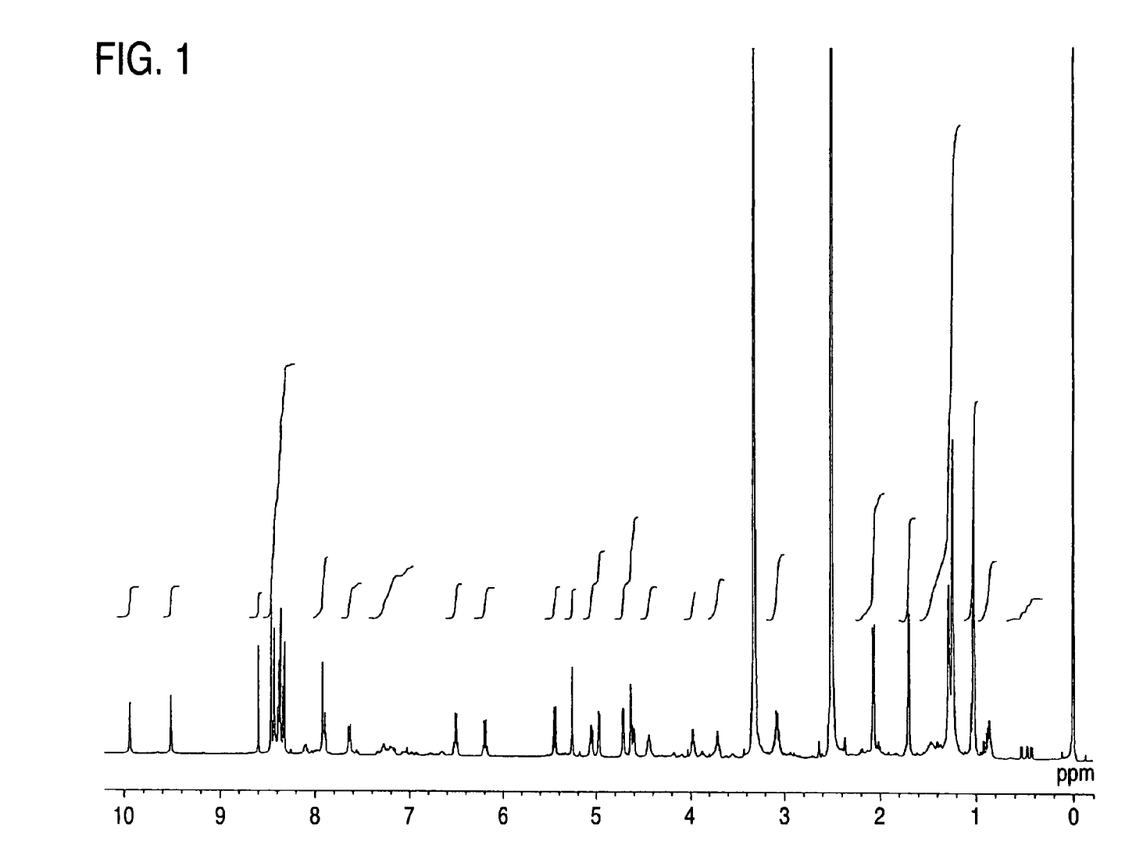
FIG. 1 is a $^1$H-NMR chart of QN3323-Y1 in DMSO-$d_6$.
Figure 2:
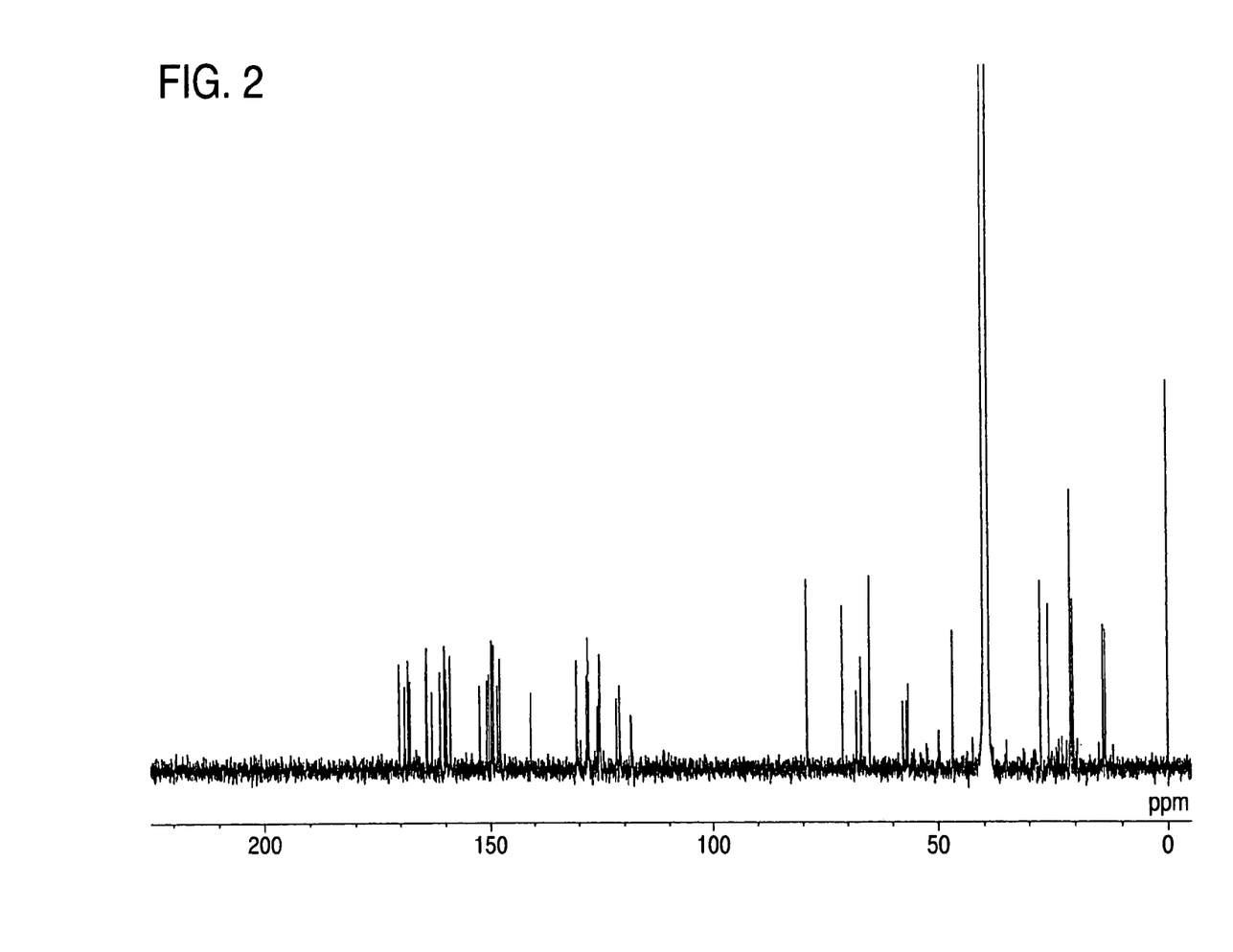
FIG. 2 is a $^{13}$C-NMR chart of QN3323-Y1 in DMSO-$d_6$.

Of the compounds that had been extracted, purified and isolated according to the process mentioned above, the physical data of the compounds of the invention QN3323-A, QN3323-B and QN3323-Y1 are given in Tables 1 to 3 and FIGS. 1 and 2. In addition, the physical data of the other isolated thiocillin I, thiocillin II and micrococcin P2 were measured, and it was confirmed that the compounds isolated herein were the same as the known compounds from those data.

TABLE 2

$^1$H-NMR and $^{13}$C-NMR Chemical Shift of QN3323-A (δ ppm)[1]

| Position | $^{13}$C | $^1$H (J/Hz) |
|---|---|---|
| 1 | 160.4 s | — |
| 2 | 148.7 s | — |
| 3 | 125.5 d | 8.37 s |
| 4 | 167.8 s | — |
| 5 | 57.2 d | 5.46 m |
| 5-NH | — | 8.32 m |
| 6 | 159.7 s | — |
| 7 | 148.3 s | — |
| 8 | 124.6 d | 8.25 s |
| 9 | 166.7 s | — |
| 10 | 129.3 s | — |
| 10-NH | — | 9.71 s |
| 11 | 168.5 s | — |
| 12 | 56.7 d | 4.71 m |
| 12-NH | — | 7.60 s |
| 13 | 159.7 s | — |
| 14 | 149.8 s | — |
| 15 | 125.7 d | 8.46 s |
| 16 | 164.2 s | — |
| 17 | 128.3 s | — |
| 18 | 149.6 or 151.0 s | — |
| 19 | 152.9 s | — |
| 20 | 120.6 d | 7.98 s |
| 21 | 170.4 s | — |
| 22 | 56.6 d | 5.05 m |
| 22-NH |  | 8.37 m |
| 23 | 140.8 d | 8.42 d (12.0) |
| 24 | 118.5 d | 8.33 d (6.0) |
| 25 | 149.6 or 151.0 s | — |
| 26 | 168.2 s | — |
| 27 | 121.6 d | 8.59 s |
| 28 | 149.3 s | — |
| 29 | 161.3 s | — |
| 30 | 125.4 d | 8.47 s |
| 31 | 150.2 s | — |
| 32 | 159.1 s | — |
| 32-NH | — | 9.60 s |
| 33 | 130.1 s | — |
| 34 | 164.4 s | — |
| 34-NH | — | 8.30 s |
| 35 | 49.5 t | 3.89 m |
| 36 | 205.2 s | — |
| 37 | 26.8 q | 2.09 s |
| 38 | 66.9 d | 3.97 m |

TABLE 1

Physicochemical properties of QN3323-A and QN3323-B

| | QN3323-A | QN3323-B | QN3323-Y1 |
|---|---|---|---|
| Property | Colorless powder | Colorless powder | |
| Melting point (dec.) | >220° C. | >220° C. | |
| $[\alpha]_D^{25}$ (MeOH) | 64.7° (c0.37) | 60.9° (c 0.15) | |
| Molecular formula | $C_{48}H_{47}N_{13}O_{10}S_6$ | $C_{49}H_{49}N_{13}O_{10}S_6$ | $C_{48}H_{49}N_{13}O_{10}S_6$ |
| Mass Spectroemtry: | | | |
| ESI-MS (M + H)$^+$ | 1158 | 1172 | 1160 |
| TOFHR-MS | | | |
| Found (m/z) | 1180.1795 (M + Na)$^+$ | 1194.1933 (M + Na)$^+$ | 1160.2130 (M + H)$^+$ |
| Calculated (m/z) | 1180.1791 (M + Na)$^+$ | 1194.1948 (M + Na)$^+$ | 1160.2128 (M + H)$^+$ |
| UV $\lambda_{max}^{MeOH}$ nm (ε) | 213 (79833), 290 (sh), 344 (14463) | 215 (100963), 290 (sh), 346 (29349) | 207 (207000), 347 (12000) |
| IR $\nu_{max}^{KBr}$cm$^{-1}$ | 3385 (OH), 1662 (CO), 1534, 1481, 754 | 3399 (OH), 1661(CO), 1533, 1481, 753 | |

TABLE 2-continued

$^1$H-NMR and $^{13}$C-NMR Chemical Shift of QN3323-A (δ ppm)[1]

| Position | $^{13}$C | $^1$H (J/Hz) |
|---|---|---|
| 39 | 20.9 q | 1.02 d (6.0) |
| 40 | 71.3 s | — |
| 41 | 25.7 q | 1.25 s |
| 42 | 27.4 q | 1.23 s |
| 43 | 128.7 d | 6.50 m |
| 44 | 13.6 q | 1.74 d (6.0) |
| 45 | 68.2 d | 4.51 m |
| 46 | 20.1 q | 1.38 d (6.0) |
| 47 | 129.0 d | 6.59 m |
| 48 | 13.4 q | 1.73 d (6.5) |

[1] Measured in DMSO-$d_6$. $^1$H-NMR, 500 MHz, and $^{13}$C-NMR, 125 MHz.

TABLE 3

$^1$H-NMR and $^{13}$C-NMR Chemical Shift of QN3323-B (δ ppm)[1]

| Position | $^{13}$C | $^1$H (J/Hz) |
|---|---|---|
| 1 | 160.4 s | — |
| 2 | 148.5 s | — |
| 3 | 126.0 d | 8.41 s |
| 4 | 168.2 s | — |
| 5 | 57.2 d | 5.52 m |
| 5-NH | — | 8.22 m |
| 6 | 159.5 s | — |
| 7 | 148.1 s | — |
| 8 | 125.0 d | 8.28 s |
| 9 | 166.9 s | — |
| 10 | 129.1 s | — |
| 10-NH | — | 9.53 s |
| 11 | 167.6 s | — |
| 12 | 56.6 d | 4.73 m |
| 12-NH | — | 7.57 s |
| 13 | 159.4 s | — |
| 14 | 150.0 s | — |
| 15 | 125.4 d | 8.46 s |
| 16 | 164.2 s | — |
| 17 | 128.6 s | — |
| 18 | 151.5 s | — |
| 19 | 153.8 s | — |
| 20 | 120.0 d | 7.97 s |
| 21 | 170.3 s | — |
| 22 | 55.2 d | 5.28 m |
| 22-NH | — | 8.11 m |
| 23 | 140.5 d | 8.46 d (6.0) |
| 24 | 118.9 d | 8.38 d (11.5) |
| 25 | 149.5 s | — |
| 26 | 168.2 s | — |
| 27 | 121.6 d | 8.58 s |
| 28 | 149.4 s | — |
| 29 | 161.3 s | — |
| 30 | 125.4 d | 8.47 s |
| 31 | 150.3 s | — |
| 32 | 159.1 s | — |
| 32-NH | — | 9.58 s |
| 33 | 130.1 s | — |
| 34 | 164.4 s | — |
| 34-NH | — | 8.30 s |
| 35 | 49.5 t | 3.89 m |
| 36 | 205.2 s | — |
| 37 | 26.8 q | 2.08 s |
| 38 | 75.6 d | 3.89 m |
| 38-OCH$_3$ | 55.6 q | 2.90 s |
| 39 | 15.5 q | 1.04 d (6.0) |
| 40 | 71.1 s | — |
| 41 | 25.6 q | 1.28 s |
| 42 | 27.4 q | 1.24 s |
| 43 | 128.6 d | 6.49 m |
| 44 | 13.9 q | 1.72 d (6.0) |
| 45 | 67.1 d | 4.46 m |
| 46 | 19.0 q | 1.44 d (6.5) |
| 47 | 129.0 d | 6.58 m |
| 48 | 13.4 q | 1.73 d (6.5) |

[1] Measured in DMSO-$d_6$. $^1$H-NMR, 500 MHz, and $^{13}$C-NMR, 125 MHz.

From the physicochemical properties listed in Tables 1 to 3 above and FIGS. 1 and 2 below, the structures of the substances have been determined to have the following formulae.

QN3323-A: R = H
QN3323-B: R = CH$_3$

-continued

QN3323-Y1

QN3323-A and QN3323-B differ from thiocillin I and thiocillin II in that the C(36)-position in the former is carbonyl. QN3323-Y1 differs from thiocillin I in that the double bond between C(10) and C(43) in the former is of E-type.

EXAMPLE 3

Antibacterial Activity:

The minimal inhibitory concentration (MIC) of the compounds of the invention obtained in Example 1, QN3323A, QN3323-B, QN3323-Y1, thiocillin I, thiocillin II and micrococcin P2 against *Staphylococcus aureus* FDA209P (*S. aureus*), *Staphylococcus epidermidis* IID866 (*S. epidezmidis*), *Enterococcus faecalis* IID682 (*E. Faecalis*) and *Enterococcus faecium* CAY09_1 (*E. faecium*), as well as against drug-resistant bacteria, *Staphylococcus aureus* CAY32001 (MRSA) (*S. aureus* (MRSA)) and *Enterococcus faecium* CAY09_2 (VRE) (*E. faecium* (VRE)) was measured according to the standard method of the Chemotherapy Society of Japan (CHEMOTHERAPY, 1981, 29(1):76, revised minimal inhibitory concentration (MIC) determination method). The cells of *S. aureus* (MRSA) were incubated at 32° C. The data obtained are shown in Table 4.

EXAMPLE 4
Remedial Effect for Infected Mouse Model

The compounds of the invention, QN3323-A, QN3323-B, thiocillin I and thiocillin II were tested using an infected mouse model to determine the effectivness thereof. Concretely, cells of *Staphylococcus aureus* Smith cultivated for 16 hours at 37° C. were suspended in 3% butamutin (by Tokyo Kasei), and the resulting cell suspension was intraabdominally infected into 4-week old male ICR(CD-1) mice (from Charles River of Japan, SPF) (about 3×10$^6$ CFU/mouse). Two hours after the infection, the compound of the invention dissolved in a solvent (10% DMSO, 10% HCO-60 (by Nikko Chemicals), 80% physiological saline), was subcutaneously administered to each mouse. On 4 to 7 days after the treatment, the mice were observed, and their ED50 value was calculated according to probit method. The data are given in Table 5.

TABLE 5

|  | ED5O (mg/kg) |
| --- | --- |
| QN3323-A | 7.6 |
| QN3323-B | 13.2 |
| Thiocillin I | 1.4 |
| Thiocillin II | 2.2 |

TABLE 4

| | MIC (μg/ml) | | | | | |
| --- | --- | --- | --- | --- | --- | --- |
| | QN3323-A | QN3323-B | QN3323-Y1 | Thiocillin I | Thiocillin II | Micrococcin P2 |
| *S. aureus* | 0.05 | 0.20 | 0.25 | | | |
| *S. epidermidis* | 0.39 | 0.20 | 0.25 | | | |
| *E. faecalis* | 1.56 | 0.78 | 0.5 | | | |
| *E. faecium* | 1.56 | 0.78 | 0.5 | | | |
| *S. aureus* (MRSA) | 1.56 | 1.56 | 2 | 0.78 | 0.10 | 0.78 |
| *E. faecium* (VRE) | 1.56 | 0.20 | 0.25 | 0.78 | 0.05 | 0.2 |

From the above, it is understood that the novel thiopeptide compounds (I') of the invention have good antibacterial activity especially even against multidrug-resistant bacteria such as MRSA and VRE, and therefore the compounds are useful for medicines, especially for antibacterial agents, more particularly for preventives and remedies for infections with multidrug-resistant bacteria. In addition, known compounds, thiocillin I, thiocillin II and micrococcin P2 have good antibacterial activity against MRSA and VRE, and are useful for preventives and remedies for infections with multidrug-resistant bacteria, especially for MRSA or VRE infections.

The invention claimed is:

1. Thiopeptide compounds of the following formula or their pharmaceutically acceptable salts:

wherein A represents CH—OH or C=O; R represents H or $CH_3$;

$R^a$ and $R^b$ each represent H or $CH_3$;

provided that when $R^a$ is H, then $R^b$ is $CH_3$; when $R^a$ is $CH_3$, then $R^b$ is H; when A is CH—OH, then $R^a$ is H and $R^b$ is $CH_3$.

2. Compounds or their pharmaceutically acceptable salts as claimed in claim 1, wherein A is C=O, R is H, $R^a$ is $CH_3$, and $R^b$ is H.

3. Compounds or their pharmaceutically acceptable salts as claimed in claim 1, wherein A is C=O, R is $CH_3$, $R^a$ is $CH_3$, and $R^b$ is H.

4. Compounds or their pharmaceutically acceptable salts as claimed in claim 1, wherein A is CR—OH, R is H, $R^a$ is H, and $R^b$ is $CH_3$.

5. A pharmaceutical composition that comprises, as the active ingredient thereof, a compound of claim 1 or its pharmaceutically acceptable salt and a pharmaceutically acceptable carrier.

6. The pharmaceutical composition as claimed in claim 5, which is an antibacterial agent.

7. A method for producing thiopeptide compounds of formula (I'), which comprises cultivating cells of *Bacillus* sp. QN03323 (FERM BP-7864) followed by collecting the thiopeptide compounds of claim 1 from the resulting culture.

8. A method for treating infections caused by multidrug-resistant bacteria, which comprises administering to a patient in need thereof an effective amount of a thiopeptide compound of the following formula I' or a pharmaceutically acceptable salt thereof:

wherein A represents CH—OH or C=O; R represents H or $CH_3$;
$R^a$ and $R^b$ each represent H or $CH_3$;
provided that when $R^a$ is H, then $R^b$ is $CH_3$, when $R^a$ is $CH_3$, then $R^b$ is H; when A is CH—OH, then $R^a$ is H and $R^b$ is $CH_3$.

9. The method as claimed in claim 8, which is for treating infections caused by methicillin-resistant *Staphylococcus aureus* or vancomycin-resistant *Enterococcus*.

* * * * *